(12) United States Patent
Wallace et al.

(10) Patent No.: US 10,960,120 B2
(45) Date of Patent: Mar. 30, 2021

(54) DIALYSIS MACHINE

(71) Applicant: Quanta Fluid Solutions Ltd., Alcester (GB)

(72) Inventors: Mark Wallace, Kinver (GB); Ben Higgitt, Redditch (GB)

(73) Assignee: QUANTA DIALYSIS TECHNOLOGIES LIMITED, Warwickshire (GB)

( * ) Notice: Subject to any disclaimer, the term of this patent is extended or adjusted under 35 U.S.C. 154(b) by 1828 days.

(21) Appl. No.: 14/373,591

(22) PCT Filed: Jan. 28, 2013

(86) PCT No.: PCT/GB2013/000032
§ 371 (c)(1),
(2) Date: Jul. 21, 2014

(87) PCT Pub. No.: WO2013/110919
PCT Pub. Date: Aug. 1, 2013

(65) Prior Publication Data
US 2015/0027951 A1 Jan. 29, 2015

(30) Foreign Application Priority Data
Jan. 26, 2012 (GB) ...................................... 1201330

(51) Int. Cl.
*A61M 1/16* (2006.01)
(52) U.S. Cl.
CPC ............ *A61M 1/1641* (2014.02); *A61M 1/16* (2013.01); *A61M 1/1601* (2014.02);
(Continued)

(58) Field of Classification Search
CPC .............. A61M 1/1601; A61M 1/1635; A61M 1/1641; A61M 2205/3379; A61M 1/16;
(Continued)

(56) References Cited

U.S. PATENT DOCUMENTS

| 4,370,983 A | * | 2/1983 | Lichtenstein | ............ A61B 5/00 600/301 |
| 4,828,543 A | * | 5/1989 | Weiss | ...................... A61M 1/16 210/637 |

(Continued)

FOREIGN PATENT DOCUMENTS

| WO | WO 2010/027435 A1 | 3/2010 | |
| WO | WO 2011/027118 A1 * | 3/2011 | .............. F04B 43/06 |

OTHER PUBLICATIONS

May 13, 2013 International Search Report for PCT/GB2013/000032.

(Continued)

*Primary Examiner* — Patrick Orme
(74) *Attorney, Agent, or Firm* — Hahn Loeser & Parks LLP (57) ABSTRACT

A dialysis machine which monitors the pressure of blood entering and leaving a patient's body using several sensors (37, 39) and adapts the pressure of a dialysate solution feed to compensate for compliances in the dialysate fluid flow path. As a consequence, better flow balance is maintained throughout dialysis treatment leading to a more uniform removal of waste materials from the blood.

43 Claims, 9 Drawing Sheets

(52) U.S. Cl.
CPC ..... *A61M 1/1635* (2014.02); *A61M 2205/126* (2013.01); *A61M 2205/128* (2013.01); *A61M 2205/3331* (2013.01); *A61M 2205/3334* (2013.01); *A61M 2205/3344* (2013.01); *A61M 2205/3379* (2013.01)

(58) Field of Classification Search
CPC .......... A61M 1/3639; A61M 2205/126; A61M 2205/3331; A61M 2205/3334; A61M 2205/3344
See application file for complete search history.

(56) References Cited

U.S. PATENT DOCUMENTS

| | | | | |
|---|---|---|---|---|
| 4,897,184 | A * | 1/1990 | Shouldice | A61M 1/16 210/143 |
| 6,077,443 | A * | 6/2000 | Goldau | A61M 1/16 210/143 |
| 7,494,590 | B2 * | 2/2009 | Felding | A61M 1/16 210/646 |
| 7,857,976 | B2 * | 12/2010 | Bissler | A61M 1/16 210/103 |
| 2005/0000868 | A1 | 1/2005 | Weigel et al. | |
| 2007/0135758 | A1 * | 6/2007 | Childers | A61M 1/28 604/30 |
| 2007/0215545 | A1 | 9/2007 | Bissler et al. | |
| 2009/0124963 | A1 | 5/2009 | Hogard et al. | |
| 2010/0038317 | A1 | 2/2010 | Bissler et al. | |
| 2011/0163030 | A1 * | 7/2011 | Weaver | A61M 1/3641 210/637 |

OTHER PUBLICATIONS

Aug. 7, 2014 Transmittal of the International Preliminary Report on Patentability for PCT/GB2013/000032.
Dec. 6, 2016 Office Action in connection with JP 2014-553795.

* cited by examiner

Prior Art

DIALYSIS MACHINE

The present application is a § 371 submission of international application PCT/GB2013/000032, filed on 28 Jan. 2013 and published in the English language with publication number WO 2013/110919 A1 on 1 Aug. 2013, which claims the benefit of the filing date of GB 1201330.6, filed 26 Jan. 2012.

FIELD OF INVENTION

The present invention relates to dialysis machines and in particular, but not exclusively, to a disposable cartridge for use in haemodialysis machine.

BACKGROUND TO THE INVENTION

Dialysis is a treatment which replaces the renal function of removing excess fluid and waste products, such as potassium and urea, from blood. The treatment is either employed when renal function has deteriorated to an extent that uremic syndrome becomes a threat to the body's physiology (acute renal failure) or, when a longstanding renal condition impairs the performance of the kidneys (chronic renal failure).

There are two major types of dialysis, namely haemodialysis and peritoneal dialysis.

In peritoneal dialysis treatment, a dialysate solution is run through a tube into the peritoneal cavity. The fluid is left in the cavity for a period of time in order to absorb the waste products, and is subsequently removed through the tube for disposal.

It is common for patients in the early stages of treatment for a longstanding renal condition to be treated by peritoneal dialysis before progressing to haemodialysis at a later stage.

In haemodialysis, the patient's blood is removed from the body by an arterial line, is treated by the dialysis machine, and is then returned to the body by a venous line. The machine passes the blood through a dialyser containing tubes formed from a semi permeable membrane. On the exterior of the semi permeable membrane is a dialysate solution with the blood passing down the interior. The semi permeable membrane filters the waste products and excess fluid from the blood into the dialysate solution. The membrane allows the waste and a controlled volume of fluid to permeate into the dialysate whilst preventing the loss of larger more desirable molecules, like blood cells and certain proteins and polypeptides.

The action of dialysis across the membrane is achieved primarily by a combination of diffusion (the migration of molecules by random motion from a region of higher concentration to a region of lower concentration), and convection (solute movement that results from bulk movement of solvent, usually in response to differences in hydrostatic pressure).

Fluid removal (otherwise known as ultrafiltration) is achieved by reducing the hydrostatic pressure of the dialysate side of the membrane, or increasing the hydrostatic pressure on the blood side, thereby causing free water to move across the membrane along the pressure gradient.

However in order to achieve accurate flow balance (the matching of dialysate flow into and out of the dialyser) it is imperative to ensure that the machine can operate in a state in which the volume of dialysate pumped into the dialyser is the same as the volume pumped out. If this balance is not maintained then fluid from the dialysate may enter the blood or fluid from the blood may be drawn into the dialysate. If the balance of flow into and out of the dialyser is not accurately controlled unacceptable levels of mass transfer to or from the patient may occur.

However, no two pumps are likely to pump exactly the same volume and consequently the use of a designated upstream pump and a volumetrically matched downstream pump can introduce error into the flow balance system due to the manufacturing tolerances of the two pumps. Again, these tolerances may potentially lead to unacceptable levels of mass transfer to or from the patient.

It is known to swap the upstream and downstream pumps over a number of pump cycles in order to balance out any tolerance error in the manufactured volume of the pumps. This is effective at balancing the pumped volume, but does not address any imbalance caused by the valves that control fluid flow between the pumps, the dialyser and the patient. Any system implementing a switching of the pumps upstream and downstream of the dialyser requires the use of two inlet valves and two outlet valves per pump in order that the pumps may be swapped. These valves cannot be readily switched in a similar manner to the pumps, and since no two valves are the same, volumetric inaccuracy is inevitably introduced into the system by virtue of the manufacturing tolerances in the valve and connection between the valve and the pump.

Furthermore in a system using a mechanically or pneumatically operated flexible film to operate the pumps and valves the variation in membrane position upon actuation leads to inaccuracies in the volume of fluid displaced during the actuation of the valve.

A solution to this problem is to use check valves which do not displace any liquid during operation.

However, whilst this is practical in a conventional, fixed installation machine, it is not possible to implement such valves in a disposable system where the walls and valves of the fluid pathway are not fully constrained to give a constant fixed volume.

It is an object of the present invention to provide a haemodialysis device which at least mitigates some of the problems described above.

SUMMARY OF THE INVENTION

According to a first aspect of the invention there is provided a dialysis device, the device including an arterial blood line for delivering patient blood to a dialyser, a venous blood line for returning dialysed blood from the dialyser to the patient, a controller which controls a dialysate distribution pump for pumping fresh dialysate into the dialyser and spent dialysate out of the dialyser, the dialysate distribution pump having an inlet line for receiving fresh dialysate from a dialysate supply, the device further including a pressure sensor in the arterial and/or venous blood line, the sensor operably connected to the controller such that the controller receives a signal from the sensor representative of the pressure in the arterial and/or venous blood line, wherein the controller monitors the signal from the sensor in the arterial and/or venous blood line and controls the pressure of the dialysate in the inlet line of the dialysate distribution pump in response to the pressure measured in the arterial and/or venous blood line by generating at least one control signal.

Since the arterial and/or venous blood line pressures vary during the course of a treatment, for example by variation in patient blood pressure or by patient venous and arterial access elevation, it follows that the pressures in the dialysate line at the inlet and outlet to the dialyser also vary by way of pressure transfer across the dialyser from the blood line to the dialysate line. This causes inaccuracies in flow balance over the course of a treatment in prior art devices.

Advantageously, in the present invention, the control of the pressure of the dialysate in the dialysate distribution pump inlet line in proportion to the blood line pressures acts to mitigate the variance in the position of the compliant structures in the fluid line. This in turn ensures the volumetric balance of the dialysate fluid entering and leaving the dialyser thereby improving flow balance accuracy.

In prior art machines which have a fixed dialysate distribution inlet line pressure, and consequently a varying pressure in the dialysate line at the inlet and outlet to the dialyser (caused by variance in blood line pressures passing across the dialyser), the pressure difference across any compliant structures in the fluid line will vary. Compliant structures can include valves which displace a volume of fluid upon opening and closing which is proportional to the pressure difference across the valve. The fluid lines themselves can also have a degree of compliancy, as can the pumps.

Thus the swept volume of the compliant members, that is to say the variation in the volume of the compliant members between a low pressure difference across the member and a high pressure difference, can be significant. The accumulation of the variation in position of the compliant structures in the flow path can lead to significant flow balance error over the course of a treatment due to a discrepancy in the volume of fluid pumped into the dialyser and the volume of fluid pumped out of the dialyser.

In contrast, in the present invention, the controlling of the pressure on the dialysate side of the dialyser in proportion to the pressure on the blood side ensures that the variation in the swept volume of any compliant structures in the dialysate flow path is dramatically reduced which significantly reduces flow balance error. This in turn improves the effectiveness of the treatment.

Alternatively, the controller may be configured to control the pressure of the dialysate in the inlet line of the dialysate distribution pump by changing the hydraulic resistance of at least a portion of the flow path. This may typically done through compression and/or expansion of the compliant structures in the flow path such as channels, tubes, valves or combinations thereof. Most typically, this variation in hydraulic resistance is effected by compression of the tubes linking the dialysate supply pump and the dialysate distribution pump.

This allows the pressure of the dialysate in the inlet line of the dialysate distribution pump to be varied without modifying the movements of the pumps. The controller may be connected to one or more clamping means adapted to compress the tubing of the device to obtain the desired pressure.

Preferably, the dialysate distribution pump is a flow balance pump for matching the volume of dialysate pumped into and out of the dialyser. Preferably, the flow balance pump has a first pump chamber for pumping dialysate into the dialyser and a second pump chamber for pumping dialysate out of the dialyser.

Preferably, the device includes a dialysate supply pump having an outlet fluidically connected to the inlet line of the dialysate distribution pump, the dialysate supply pump being capable of pumping dialysate into the inlet line of the dialysate distribution pump at a predetermined pumping pressure set by the controller in response to the pressure measured in the arterial and/or venous blood line.

Advantageously, the dialysate supply pump pumps dialysate into the inlet line of the dialysate distribution pump at a pressure determined by the controller in response to the pressure measured in the arterial and/or venous blood line. This balances the pressures difference across compliant structures in the fluid line, resulting in improved accuracy of flow balance across the dialyser.

Preferably, the inlet line of the dialysate distribution pump is fluidically connected to the first pump chamber. Preferably, the device has a valve in the inlet line of the dialysate distribution pump situated fluidically between the dialysate supply pump and the dialysate distribution pump.

Preferably, the controller controls the predetermined pumping pressure in order to achieve a predetermined valve closure pressure in the inlet line upon closure of the valve.

Alternatively, the controller controls a residual pressure in the inlet line of the dialysate distribution pump after completion of an outlet stroke of the dialysate distribution pump in order to achieve a predetermined valve closure pressure in the inlet line upon closure of the valve.

Advantageously, this feature of the invention allows the pumping pressure of the dialysate supply pump to be set independently from the pressure sensed in the blood lines. In this embodiment, the residual pressure (that is to say the pressure in the inlet line after completion of the outlet stroke of the pump) is set in response to the blood line pressures in contrast to the setting of the pumping pressure during the outlet stroke. Thus the residual pressure is set to the predetermined valve closure pressure after completion of the outlet stroke of the dialysate supply pump. In this way the dialysate supply pump can pump dialysate at a pumping pressure which differs from the predetermined pumping pressure of the alternative embodiment. For example a higher pumping pressure can be set by the controller in order to achieve a higher flow rate, the controller then setting the residual pumping pressure to a lower value upon (that is to say just before or at the same time as) closure of the valve. In this way higher flow rates can be achieved without any subsequent flow balance errors resulting from inconsistencies in the swept volume of the compliant structures described above.

Preferably, the dialysate supply pump is a membrane pump having a pump cavity covered by a flexible membrane, wherein the pump is operable by actuation of the membrane. Preferably, the dialysate supply pump has an inlet stroke in which dialysate is drawn into the pump from a dialysate supply, and an outlet stroke in which dialysate is pumped into the inlet line of the dialysate distribution pump.

Preferably, the first chamber of the flow balance pump is a membrane pump having a pump cavity covered by a flexible membrane, wherein the pump is operable by actuation of the membrane.

Preferably, the second chamber of the flow balance pump is a membrane pump having a pump cavity covered by a flexible membrane, wherein the pump is operable by actuation of the membrane.

Preferably, the first chamber of the flow balance pump has an inlet stroke in which dialysate is drawn from the dialysate supply pump, and an outlet stroke in which dialysate is pumped into the dialyser.

Preferably, the second chamber of the flow balance pump has an inlet stroke in which dialysate is drawn from the dialyser and an outlet stroke in which dialysate is pumped to drain. Preferably, the membrane pump is pneumatically actuable.

Preferably, the predetermined pumping pressure of the dialysate supply pump is controlled by altering the pneumatic pressure applied to the membrane to actuate the pump.

Preferably the predetermined residual pressure in the inlet line is controlled by altering the pneumatic pressure applied to the membrane after completion of the outlet stroke. Preferably the pressure sensor in the arterial line is situated downstream of a blood pump for pumping blood from the patient to the dialyser. Preferably the pressure sensor is situated in the venous line.

According to a second aspect of the invention there is provided a method of operating a dialysis machine, the method including the steps of providing an arterial blood line for delivering patient blood to a dialyser, a venous blood line for returning dialysed blood from the dialyser to the patient, a dialysate distribution pump for pumping fresh dialysate into the dialyser and spent dialysate out of the dialyser, the dialysate distribution pump having an inlet line for receiving fresh dialysate from a dialysate supply, the method further including the steps of: monitoring the pressure of blood in the arterial blood line and/or the pressure of blood in the venous line, controlling the pressure of the dialysate in the inlet line of the dialysate distribution pump in response to the pressure measured in the arterial and/or venous blood line.

Preferably, the dialysate distribution pump is a flow balance pump for matching the volume of dialysate pumped into and out of the dialyser. Preferably, the flow balance pump has a first pump chamber for pumping dialysate into the dialyser and a second pump chamber for pumping dialysate out of the dialyser.

Preferably, the method includes the further steps of providing a dialysate supply pump having an outlet fluidically connected to the inlet line of the dialysate distribution pump, and the dialysate supply pump pumping dialysate into the inlet line of the dialysate distribution pump at a predetermined pumping pressure set by the controller in response to the pressure measured in the arterial and/or venous blood line.

Preferably, the inlet line of the dialysate distribution pump is fluidically connected to the first pump chamber. Preferably, the method includes the further step of providing a valve in the inlet line of the dialysate distribution pump situated fluidically between the dialysate supply pump and the dialysate distribution pump.

Preferably, the method includes the further step of controlling the predetermined pumping pressure in order to achieve a predetermined valve closure pressure in the inlet line upon closure of the valve.

Alternatively, the method includes the further step of controlling a residual pressure in the inlet line of the dialysate distribution pump after completion of an outlet stroke of the dialysate distribution pump in order to achieve a predetermined valve closure pressure in the inlet line upon before or at the same time as closure of the valve.

Preferably, the dialysate supply pump has an inlet stroke in which dialysate is drawn into the pump from a dialysate supply, and an outlet stroke in which dialysate is pumped into the inlet line of the dialysate distribution pump.

Preferably, the first chamber of the flow balance pump is a membrane pump having a pump cavity covered by a flexible membrane, wherein the pump is operable by actuation of the membrane. Preferably, the second chamber of the flow balance pump is a membrane pump having a pump cavity covered by a flexible membrane, wherein the pump is operable by actuation of the membrane. Preferably, the first chamber of the flow balance pump has an inlet stroke in which dialysate is drawn from the dialysate supply pump, and an outlet stroke in which dialysate is pumped into the dialyser.

Preferably, the second chamber of the flow balance pump has an inlet stroke in which dialysate is drawn from the dialyser and an outlet stroke in which dialysate is pumped to drain. Preferably, the membrane pump is pneumatically actuable. Preferably, the method includes the further step of controlling the predetermined pumping pressure of the dialysate supply pump by setting the pneumatic pressure applied to the membrane to actuate the pump.

Alternatively, the method includes the further step of controlling the predetermined residual pressure in the inlet line by setting the pneumatic pressure applied to the membrane after completion of the outlet stroke.

There is provided in a third aspect of the invention, a computer program product which, when executed by a controller in communication with a dialysis machine, causes the controller to perform a method according the second aspect of the invention.

According to a fourth aspect of the invention, there is provided a method of performing dialysis comprising the steps of: delivering patient blood and fresh dialysate to a dialyser; monitoring the pressure of blood in a arterial blood line and/or the pressure of blood in a venous blood line; controlling the pressure of the dialysate in the inlet line of a dialysate distribution pump in response to the pressure measured in the arterial and/or venous blood line; and returning dialysed blood to the patient and removing spent dialysate.

According to a fifth aspect of the invention, there is provided a system comprising a dialysis machine according to the first aspect of the invention and a processor and/or a memory configured to receive data corresponding to pressure in the arterial and/or venous bloodline; and control the pressure of dialysate in a inlet line of a dialysate distribution pump in response to the pressure in the arterial and/or venous blood lines.

BRIEF DESCRIPTION OF THE DRAWINGS

The invention will now be described, by way of example only, and with reference to the following drawings, in which.

DESCRIPTION

Figure 1:
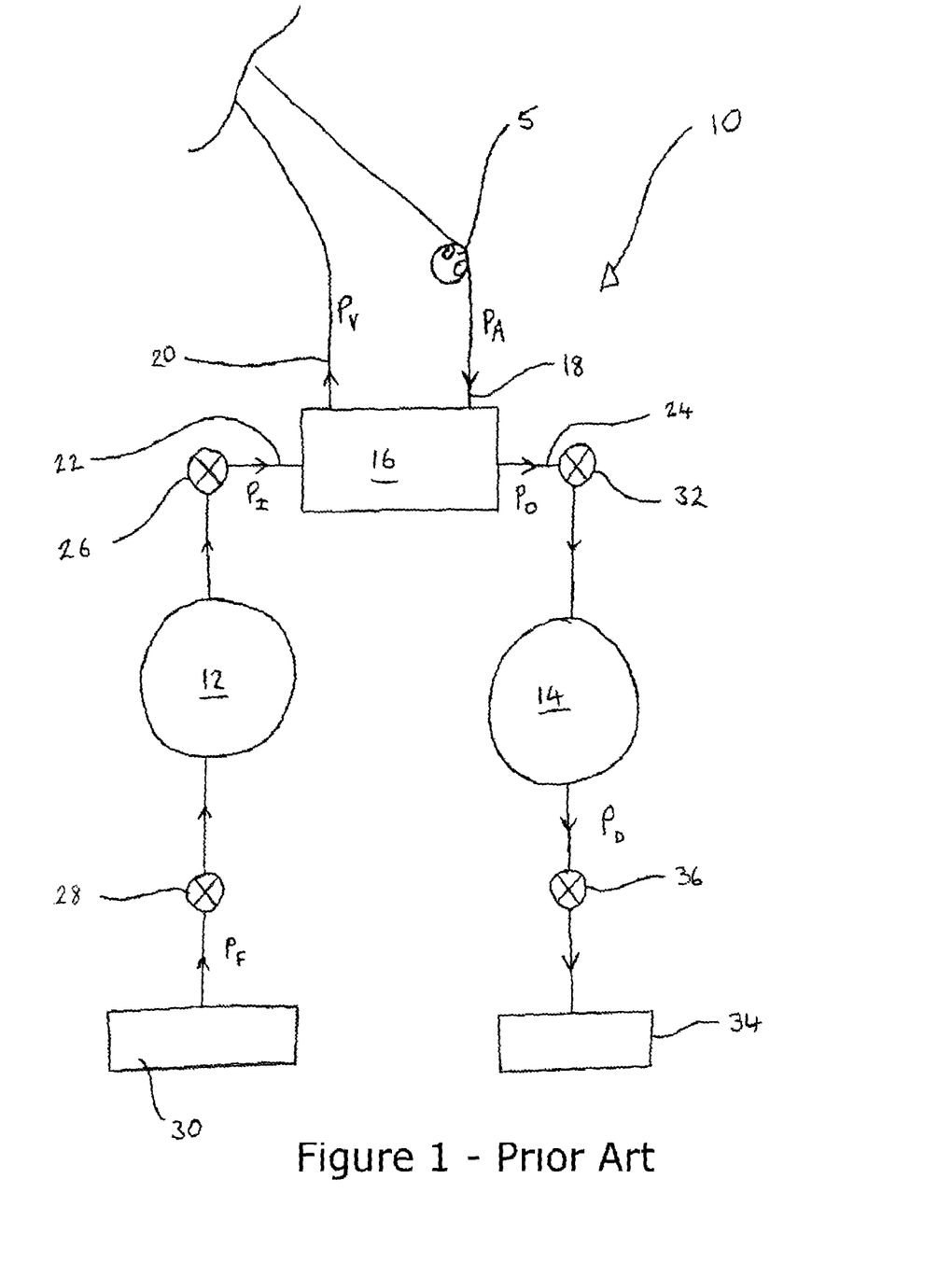
FIG. 1 is a schematic view of a prior art dialysis system.

Referring to FIG. 1, a dialysis system 10 is shown having a dialysate distribution pump in the form of a flow balance pump having a first flow balance chamber 12 and a second flow balance chamber 14. A dialyser 16 receives blood via an arterial line 18 connected to the patient by a vascular access device (not shown for clarity). The blood is pumped from the patient to the dialyser by a pump 5, typically a peristaltic pump. The blood passes through the dialyser in a known manner and is returned to the patient via a venous line 20. The dialyser 16 also has a dialysate inlet line 22 for receiving fresh dialysate and a dialysate outlet line 24 for removing the spent dialysate from the dialyser 16. In this way the waste products in the blood pass into the dialysate across a semi permeable membrane in a known manner.

Upstream of the dialysate inlet line 22 is a dialyser inlet valve 26 which controls the passage of dialysate into the dialyser 16. Dialysate is pumped into the dialyser 16 via the dialyser inlet valve 26 by the first flow balance pump 12. Upstream of the first flow balance pump chamber 12 is a flow balance pump inlet valve 28. The first flow balance pump chamber 12 is configured to draw dialysate from a dialysate source 30 via the flow balance pump inlet valve 28.

On the dialysate outlet side of the dialyser 16 is a dialysate outlet valve 32 which controls the flow of spent dialysate in the dialysate outlet line 24. The second flow balance pump chamber 14 draws spent dialysate through the dialysate outlet valve 32 and to a drain 34 via a flow balance pump outlet valve 36.

In use the flow balance pump inlet valve 28 is opened and the first flow balance pump chamber 12 is actuated to draw dialysate fluid from the dialysate source 30 into the first flow balance pump chamber 12. The flow balance pump inlet valve 28 is then closed, the dialyser inlet valve 26 opened and the first flow balance pump chamber 12 is actuated to pump dialysate into the dialyser 16.

At the same time as the first flow balance pump 12 chamber, flow balance pump inlet valve 28 and dialyser inlet valve 26 are being operated upstream of the dialyser to pump dialysate into the dialyser 16, the second flow balance pump chamber 14, dialysate outlet valve 32 and flow balance pump outlet valve 36 are operated as follows to draw dialysate form the dialyser 16.

The dialysate outlet valve 32 is opened and the second flow balance pump chamber 14 is actuated in order to draw dialysate from the dialyser 16 into the second flow balance pump chamber 14. The dialysate outlet valve 32 is then closed, the flow balance pump outlet valve 36 opened and the second flow balance pump chamber 14 is actuated to pump dialysate from the second flow balance pump chamber 14 to the drain 34.

This cycle of pumping is then repeated in order to draw a constant flow of dialysate from the dialysate source 30, through the dialyser 16 and to the drain 34.

Figure 2:
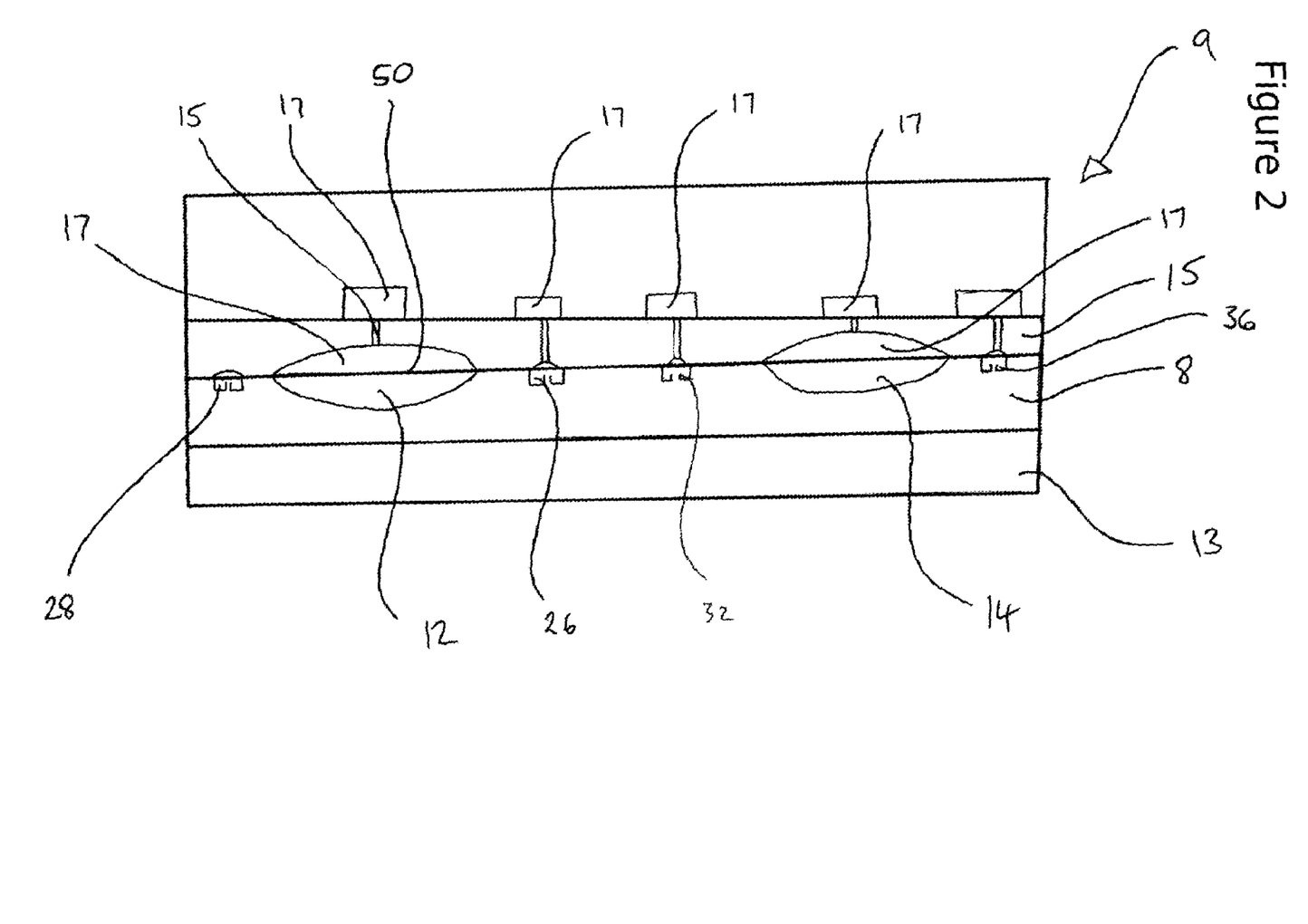
FIG. 2 is a sectioned side view of a dialysis machine of the present invention.
Figure 3:
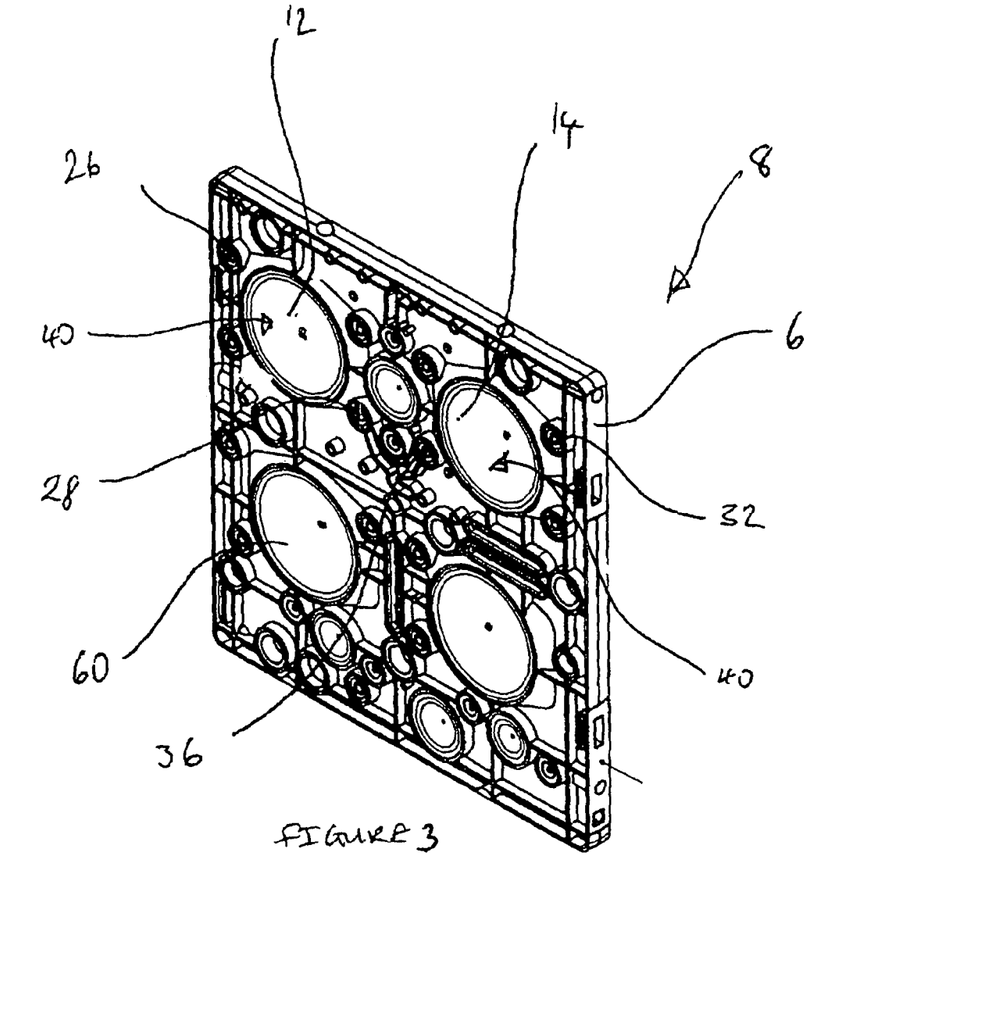
FIG. 3 is an isometric view of a dialysis cartridge of the machine of FIG. 2.

The dialysis system described above is embodied by a dialysis machine shown schematically at 9 in FIG. 2. The machine 9 includes the features of the prior art system described above and features of the present invention that will be described shortly. The machine operates a cartridge 8 (see FIG. 3) which in part embodies the pump chambers 12, 14 and valves 26, 28, 32, 36 as will be seen in further detail shortly. The cartridge 8 has a rigid body 6 covered by a flexible film 50 (shown in FIG. 2 only). The pump chambers 12, 14 are in part defined by concave pump cavities 40 formed by the body 6 of the cartridge.

In use the cartridge 8 is retained between a first platen 13 on one side of the cartridge and a second platen 15 on a second side of the cartridge. The second platen 15 defines cavities 17 which match the concave pump cavities 40 on the cartridge. The pumps are operated by pneumatically actuating the film 50 in order to draw fluid into and out of the pump chambers. This is achieved by pneumatic actuators 17 applying pressure and vacuum to the film 50 via channels 15 in a known manner. Similarly the valves 26, 28, 30, 32 are operated by pneumatic-actuators 17. A controller (not shown for clarity) controls the actuators 17 to open and close the valves and operate the pumps as will be described in further detail shortly.

Figure 4:
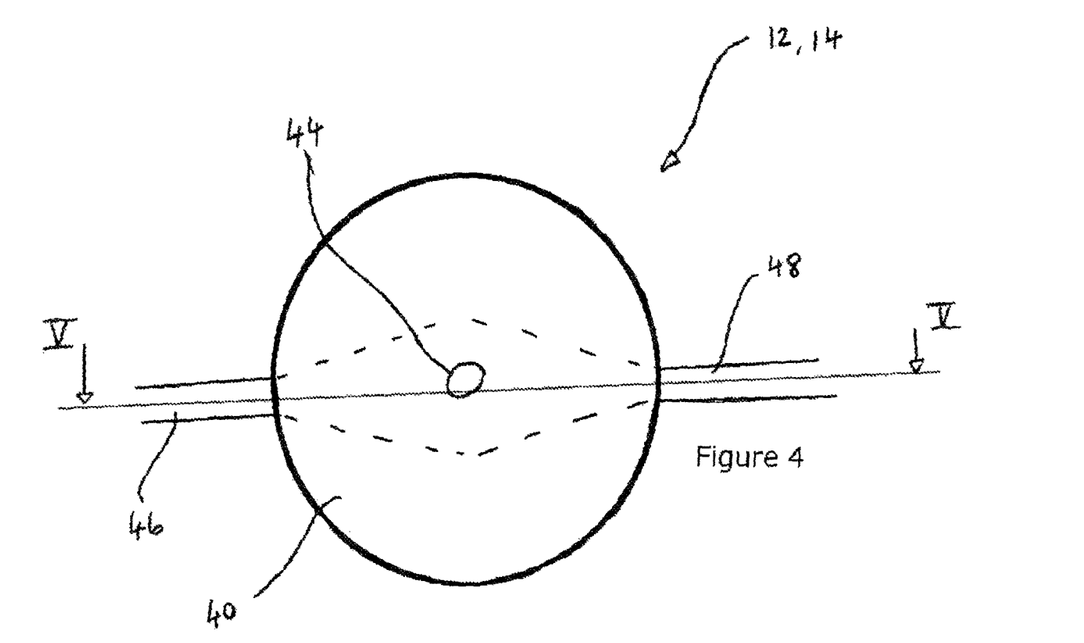
FIG. 4 is a plan view of a portion of the cartridge of FIG. 3, showing the pump chamber in greater detail.
Figure 5:
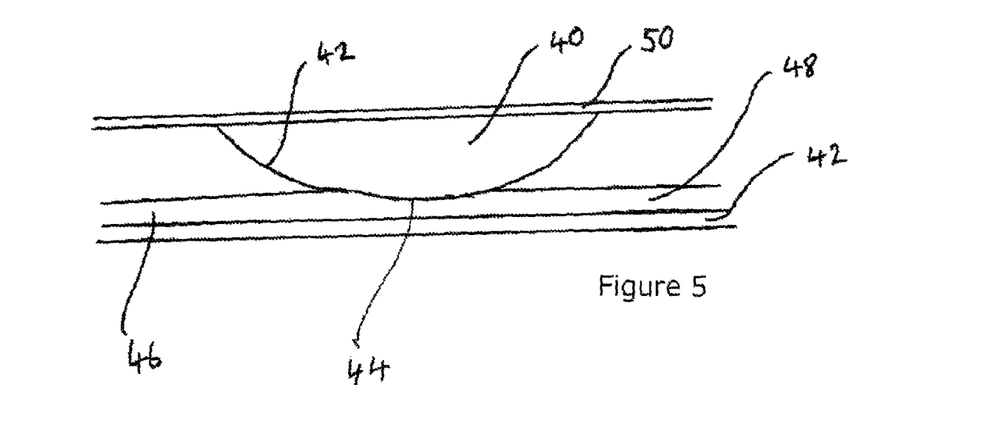
FIG. 5 is a sectioned side view along line V-V of the pump chamber of FIG. 4.

Referring now to FIGS. 4 and 5, the first and second flow balance pump chambers 12, 14 are shown in more detail. The pump cavity 40 has a lower wall 42 which defines an aperture 44 which allows access to the pump cavity 40 via the pump inlet 46 and pump outlet 48. In the first flow balance pump chamber 12 the pump inlet 46 is fluidically connected to the flow balance pump inlet valve 28 and the pump outlet 48 to the dialyser inlet valve 26. In the second flow balance pump chamber 14 the pump inlet 46 is fluidically connected to the dialysate outlet valve 32 and the pump outlet 48 to the flow balance pump outlet valve 36.

The pump cavity 40 is enclosed by the flexible film 50 which is actuated by the actuator 17 applying pressure, or vacuum, to the outer surface of the film 50. When the actuator applies a vacuum to the film, the film moves into the cavity 17 in the platen 15 (see FIG. 2) thereby drawing dialysate into the pump chamber. This is referred to as the inlet stroke of the pump. The inlet valve 28, 32 is then closed, the outlet valve 26, 36 opened and pressure applied to the film 50 in order to pump the dialysate out of the pump cavity and through the outlet valve (the outlet stroke of the pump). Once the pump has expelled the dialysate (or a predetermined proportion thereof) from the pump cavity 40, the actuator stops applying the pneumatic pressure to the film and the outlet valve is closed a predetermined fixed period of time after completion of the outlet stroke. This process is then repeated by reciprocating the film under pressure and vacuum to pump dialysate through the pump.

Figure 6:
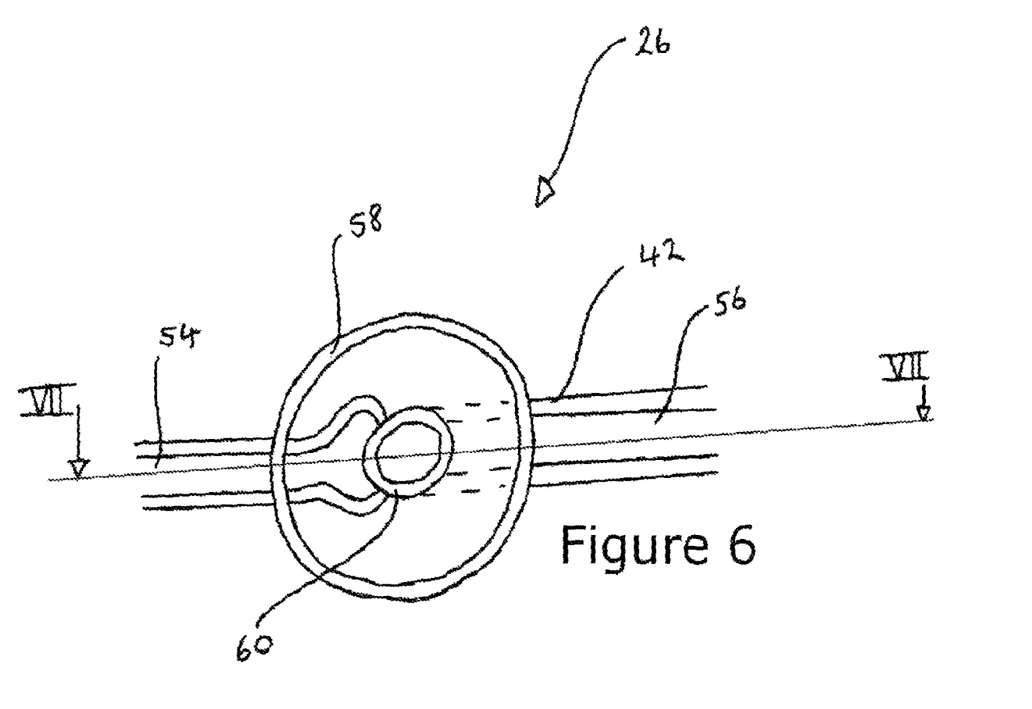
FIG. 6 is a plan view of a portion of the cartridge of FIG. 3, showing the valve in greater detail.
Figure 7:
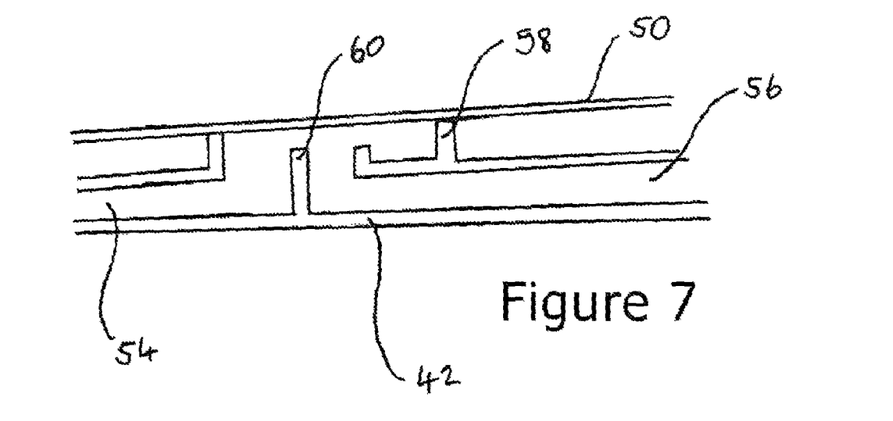
FIG. 7 is a sectioned side view along line VII-VII of the valve of FIG. 6, with the valve in its open position.

Referring now to FIGS. 6 and 7, the dialyser inlet valve 26 is shown in greater detail but the description applies equally to all of the valves 26, 28, 32, 36 which are essentially identical. The valve 26 is defined by the rigid body 9 of the cartridge 8 shown in FIG. 2. Each valve has an inlet 54 and an outlet 56. The valve has an outer upstanding wall 58 and an inner upstanding wall 60. The inner upstanding wall 60 stands slightly lower than the outer upstanding wall 58. The valve is covered by the same flexible film 50 as the pumps 12, 14 and the film 50 is pneumatically actuable by actuators 17 in a similar manner to open and close the valves as will be described in further detail below. In FIG. 7 the valve is shown in its open position in which dialysate can enter the valve via the inlet 54, pass over the inner upstanding wall 60 and out of the outlet 56.

Figure 8:
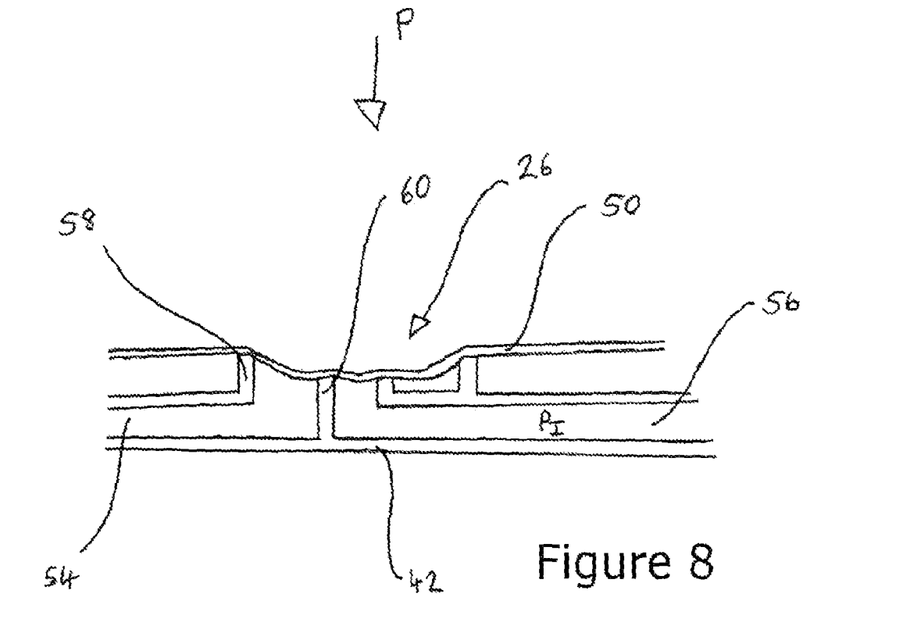
FIG. 8 is a sectioned side view along line VII-VII of the valve of FIG. 6, with the valve in its first closed position.

Turning now to FIG. 8, the valve is shown in a first closed position in which the film 50 has been actuated by the application of pressure by actuator 17 to the outer surface of the film in known manner. This application of pressure P has caused the film 50 to deflect causing the film contact the inner upstanding wall 60 thus creating a barrier between the inlet 54 and outlet 56.

Referring briefly to FIG. 1, The outlet 56 of the dialyser inlet valve 26 is subject to a pressure $P_1$. As the patient blood pressure varies during the treatment the arterial line inlet pressure $P_A$ and the venous line pressure $P_V$ vary accordingly. This variation in pressure is passed across the semi permeable membrane in the dialyser 12 to cause the pressure $P_1$ in the outlet 56 of the dialyser inlet valve 26 to vary.

Figure 9:
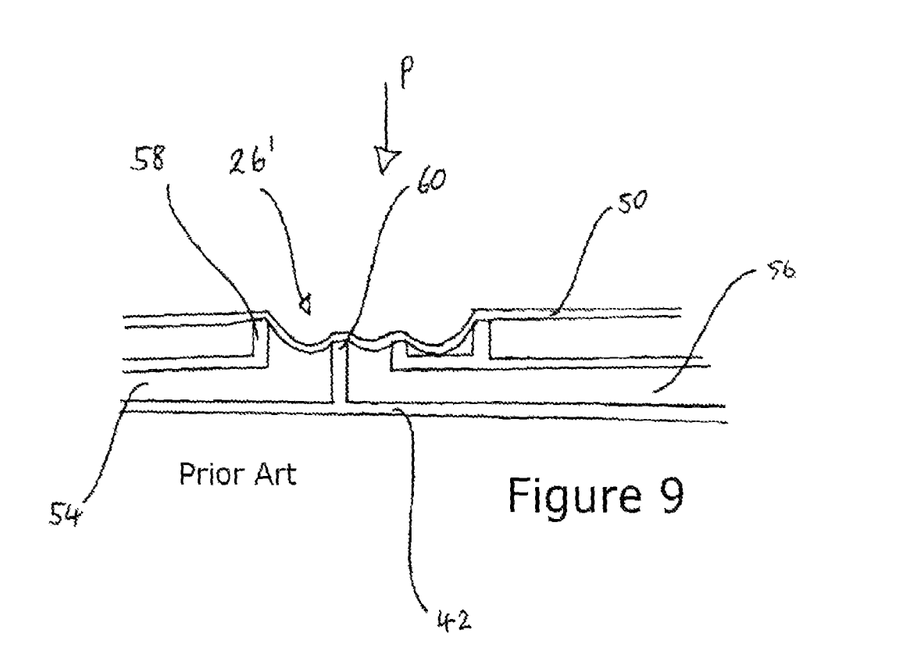
FIG. 9 is a sectioned side view along line VII-VII of the valve of FIG. 6, with the valve in its second closed position.

Turning now to FIG. 9, the effects of this variation on the valve 26 is shown. The valve 26 is the same as the valve 26 shown in FIG. 8. The difference is that the film 50 has deflected further than the position shown in FIG. 8 despite the same pressure P being applied to the outer surface of the film 50.

This variation in the deflection position of the film 50 upon actuation of the film 50 results in the swept volume of the valve 26, that is to say the volume of dialysate displaced downstream by the actuation of the valve 26, varying in an unpredictable manner throughout the treatment in prior art devices. This same effect is experienced by the flow balance pump inlet valve 28 and the dialysate outlet valve 32 with the effect that the accumulation of variation of displaced volume can lead to significant flow balance errors over the duration of the treatment in prior art devices.

The present invention overcomes this error by balancing the system pressures to ensure that the closing position of the valves (and any other compliant structures in the fluid line) are normalised in the following way.

Figure 10:
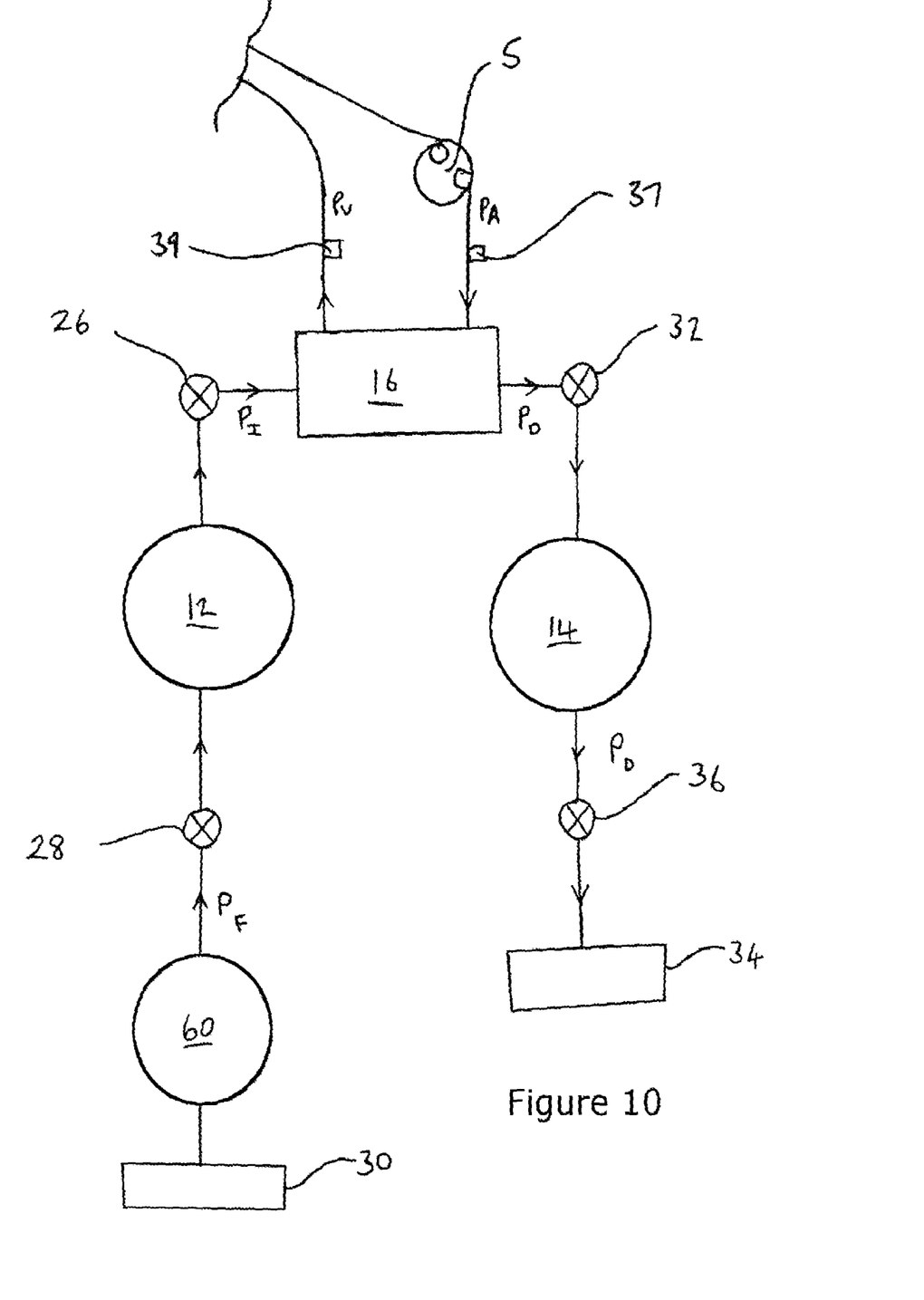
FIG. 10 is a schematic view of a dialysis system according to the present invention.

With reference to FIG. 10, the drain 34 is subject to atmospheric pressure which varies in a negligible way over the course of a treatment and can therefore be considered to be constant. The second flow balance pump chamber 14 is actuated at a constant actuation pressure throughout the treatment and accordingly the pressure difference across the flow balance pump outlet valve 36 does not vary. As a result the swept volume of the flow balance pump outlet valve 36 does not vary.

In contrast both the dialyser inlet valve 26 and dialysate outlet valve 32 are potentially subject to varying pressures $P_1$, $P_O$ at their outlet and inlet, respectively, due to the variation of arterial line inlet pressure $P_A$ and venous line pressure $P_V$. This is overcome in the present invention by a controller (not shown for clarity) monitoring the arterial line inlet pressure $P_A$ and/or the venous line pressure $P_V$ via pressure sensors 37, 39 respectively and altering the pressure $P_F$ observed by the first flow balance pump inlet valve 28 in proportion to the arterial line inlet pressure $P_A$, the venous line pressure $P_V$, or a function of both as will be described in further detail shortly. Since the arterial line inlet pressure $P_A$ and venous line pressure $P_V$ are generally proportional to one another (notwithstanding clotting in the dialyser) it is possible to control on either arterial line inlet pressure $P_A$ or venous line pressure $P_V$.

By way of an example, if the venous line pressure $P_V$ increases due to the patient elevating his or her arm, $P_1$ and $P_O$ will increase by virtue of the pressure transfer across the semi permeable membrane in the dialyser. In such as circumstance the controller will increase the pressure $P_F$ in the dialysate line proportionately to the increase in $P_V$ so as to ensure that the closure position of the valves 26, 32 remains unchanged. This dramatically reduces the flow balance error over the duration of a treatment.

This variation of pressure $P_F$ is achieved by the provision of a dialysate supply pump 60 (shown also in FIG. 10, but not FIG. 2 for clarity) which is similar both in construction and operation to the first and second flow balance pumps 12, 14 with the exception that the pressure applied by the actuator 17 to the film 50 can be varied by the controller in proportion to the arterial line inlet pressure $P_A$ and/or venous line pressure $P_V$.

Figure 11:
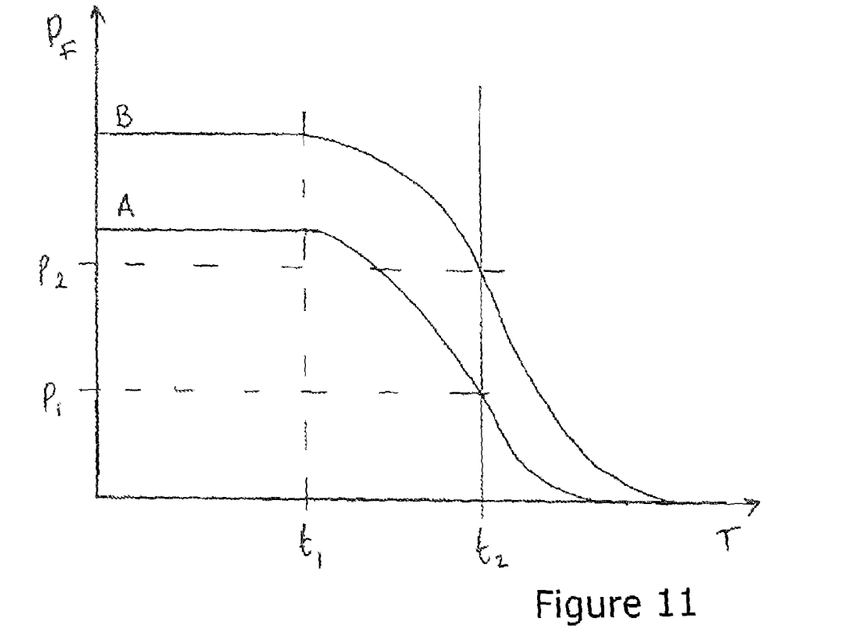
FIG. 11 is a plot of Pressure against Time as observed by the first flow balance pump inlet valve of the machine of FIG. 2 in a first embodiment of the present invention.

Referring now to FIG. 11, two plots (A, B) of pressure $P_F$ observed by the first flow balance pump inlet valve 28 are shown against time, T. It will be appreciated that $P_F$ is dictated by the pneumatic pressure applied to the film 50 by the actuator 17. In plot A, the pressure $P_F$ is initially the same as the pumping pressure, that is to say the pressure observed in the inlet dialysate line as a result of the pressure applied by the actuator 17 to the film 50 in order to actuate the pump 60. This pumping pressure is predetermined by the controller to deliver a pressure $P_1$ (the predetermined valve closure pressure) at the time of closure of the valve at $t_2$ as follows. At time $t_1$ the actuator stops applying pressure to the film 50 and the actuator vents to atmosphere, this rapidly reduces the pressure applied to the film and therefore to the pump 60. This in turn causes a decay in the pressure $P_F$ observed by the valve 28 from the predetermined pumping pressure observed during the outlet stroke of the pump. At time $t_2$ the pressure $P_F$ observed by the valve 28 has fallen to $P_1$ (the predetermined valve closure pressure) which equates to the pressure calculated by the controller in response to the arterial and/or venous pressure in order to ensure that the closure position of the valve 28 is correct.

Referring to plot B, the arterial and/or venous pressure has increased (perhaps by the patient lifting his or her arm). The controller has responded by operating the pump 60 at a higher pump pressure (the pressure applied by the actuator 17 to the film 50 in order to actuate the pump 60). This has increased the predetermined pumping pressure Pp initially observed by the valve 28. Since the time between $t_1$ (venting of the pressure applied to the pump 60) and $t_2$ (the closure of the valve 28) remains constant, the pressure $P_F$ observed by the valve 28 on closure is now $P_2$ (the predetermined valve closure pressure), the pressure required to ensure that the closure position of the valve 28 remains correct despite the increased arterial and/or venous pressure. In this way, by maintaining a constant time period between $t_1$ (venting of the pressure applied to the pump 60) and $t_2$ (the closure of the valve 28) and varying the pump pressure in the pump 60, the desired pressure $P_F$ observed by the valve 28 on closure can be maintained. The predetermined pumping pressure required to achieve a given pressure upon closure of the valve at time $t_2$ is stored by the controller in the form of look up tables. By matching the pressure observed by the valve upon closure to the arterial and/or venous pressure the variation in swept volume of the valve is minimised and flow balance accuracy thereby increased.

In an alternative embodiment of the invention the pressure $P_F$ is actively set to the required level by the time of closure of the valve 28. This allows the pump pressure to be set, for example, at a higher value during the outlet stroke of the pump chamber and then reduced at the end of the stroke to set $P_F$ to the value set by the controller as determined by the arterial or venous pressure.

Figure 12:
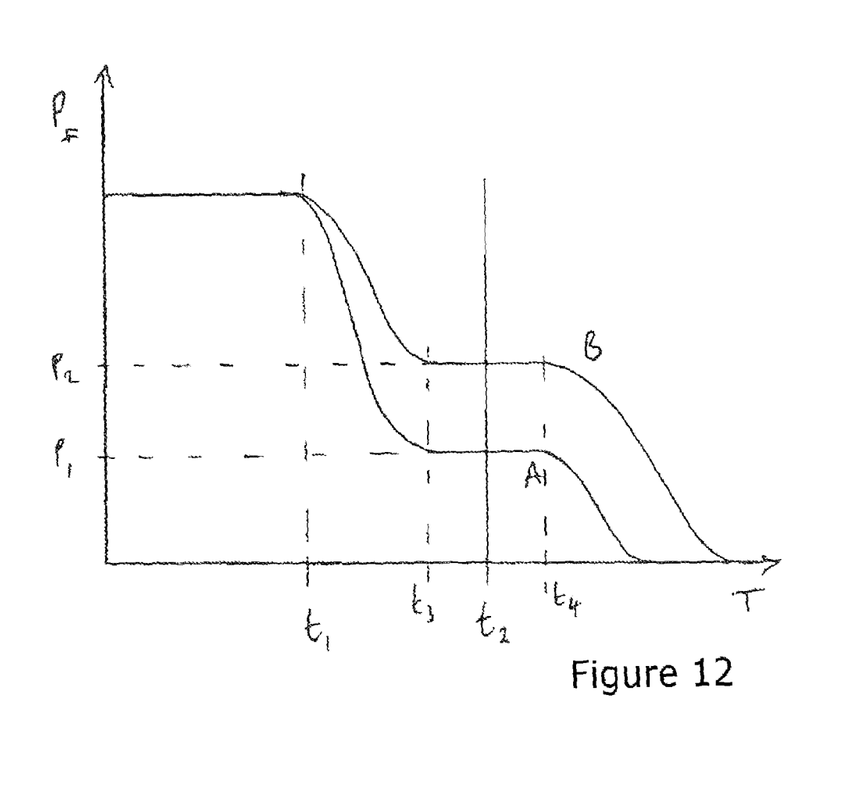
FIG. 12 is a plot of Pressure against Time as observed by the first flow balance pump inlet valve of the machine of FIG. 2 in a second embodiment of the present invention.

This is reflected in FIG. 12, in which two plots (A, B) of pressure $P_F$ observed by the first flow balance pump inlet valve 28 are shown against time, T. In this case both plots A, B start at the same pressure, namely the pressure observed in the fluid line as a result of the pressure applied by the actuator 17 to the film 50 in order to actuate the pump 60. However in this embodiment at time $t_1$ the actuator 17 does not vent to atmosphere at the end of the pump stroke. Rather the decay in the pressure $P_F$ (the residual pressure) is controlled to bring $P_F$ to the required pressure $P_1$ (referred to as the predetermined closure pressure) as quickly as possible. $P_F$ is then maintained at value $P_1$ from $t_3$ to $t_4$. This provides a longer window of time during which $P_F$ is at the predetermined valve closure pressure thereby ensuring the accuracy of $P_1$ at time $t_2$ when the valve is closed.

In the event that a higher pressure $P_F$ is required at $t_2$, the decay of the pressure applied by the actuator to the film 50 is controlled to set $P_F$ to the higher value $P_2$ between $t_3$ and $t_4$. After $t_4$ i.e. once the valve 28 has been closed the pressure applied by the actuator to the film 50 is vented to atmosphere. In this way, by varying the predetermined closure pressure $P_1$, $P_2$, the desired pressure $P_F$ observed by the valve 28 on closure can be maintained without the need to set the pumping pressure in response to arterial and/or venous pressure.

This allows the pressure at which the pump is operated during the outlet stroke (the pumping pressure) to be decoupled from the pressure observed by the valve 28. This means that the pumping pressure can be increased in order to provide increased dialysate flow rate. Furthermore the pressure at which the pump is operated can remain constant which provides for more stable conditions for the machine and cartridge leading to improved accuracy of flow balance.

Figure 13:
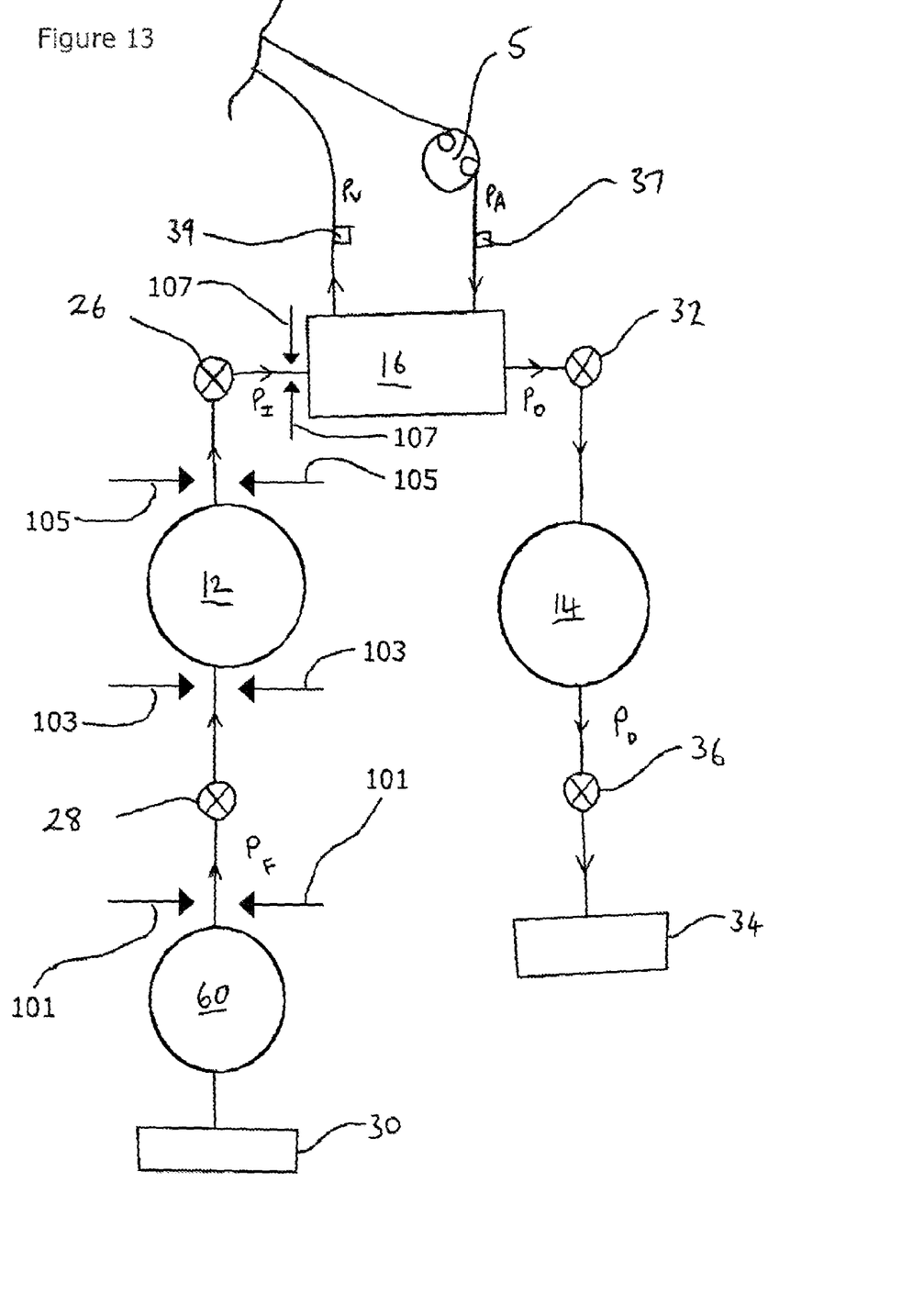
FIG. 13 is a schematic view of a further dialysis system according to the present invention.

In a further alternative embodiment the controller is connected to a clamp (not shown for clarity) or series of clamps at various positions along the fluid flow path. FIG. 13 illustrates the positions 101, 103, 105 and 107 at which a clamping force can be applied to compress the tubing containing dialysate. A clamping force is applied by the clamp at position 101 between the dialysate supply pump 60 and valve 28 down stream of the dialysate distribution pump 12. The controller controls the compression force applied by the clamps in order to vary the hydraulic resistance of the tubing and thereby moderate the pressure $P_F$ in the flow path at position 101 based on the pressure recorded by the pressure sensors 37, 39.

If a greater hydraulic resistance is required the clamping force can increase to reduce the diameter of the tubing, with the proviso that the tube remains capable of permitting fluid flow. Additional clamps can be engaged at positions 103, 105 and/or 107 to provide a greater hydraulic resistance if required.

Whilst a membrane type pump is described it is conceivable within the scope of the invention that alternative forms of pump might be used such as peristaltic pumps or syringe pumps.

The invention claimed is:

1. A dialysis device comprising:
 an arterial blood line for delivering patient blood to a dialyser;
 a venous blood line for returning dialysed blood from the dialyser to the patient;
 a dialysate distribution pump for pumping fresh dialysate into the dialyser and spent dialysate out of the dialyser, the dialysate distribution pump having an inlet line for delivering fresh dialysate to the dialysate distribution pump;
 a pressure sensor in the arterial and/or venous blood line that converts a sensed pressure to a signal representative of pressure in the arterial and/or venous blood line;
 a controller that monitors the signal from the sensor in the arterial and/or venous blood line and that is configured to generate at least one control signal in response to the signal from the sensor; and
 means for controlling pressure in the inlet line in response to the at least one control signal.

2. The device according to claim 1, wherein the controlling means comprises at least one clamp that, in response to the at least one control signal, is arranged to apply compression force to tubing at a specific position along a flow path of the fresh dialysate.

3. The device according to claim 1, wherein the dialysate distribution pump is a flow balance pump for matching volume of dialysate pumped into and out of the dialyser.

4. The device according to claim 3, wherein the flow balance pump has a first pump chamber for pumping dialysate into the dialyser and a second pump chamber for pumping dialysate out of the dialyser.

5. The device according to claim 4, wherein the inlet line of the dialysate distribution pump is fluidically connected to the first pump chamber.

6. The device according to claim 4, wherein the first pump chamber of the flow balance pump has a pump cavity covered by a flexible membrane, and is operable to pump dialysate into the dialyser by actuation of the membrane.

7. The device according to claim 4, wherein the second pump chamber of the flow balance pump has a pump cavity covered by a flexible membrane, and is operable to pump dialysate out of the dialyser by actuation of the membrane.

8. The device according to claim 4, wherein the first pump chamber of the flow balance pump has an inlet stroke in which dialysate is drawn from a dialysate supply pump, and an outlet stroke in which dialysate is pumped into the dialyser.

9. The device according to claim 4, wherein the second pump chamber of the flow balance pump has an inlet stroke in which dialysate is drawn from the dialyser and an outlet stroke in which dialysate is pumped to drain.

10. The device according to claim 1, wherein the controlling means comprises a dialysate supply pump having an outlet fluidically connected to the inlet line of the dialysate distribution pump, the dialysate supply pump being capable of pumping dialysate into the inlet line of the dialysate distribution pump at a predetermined pumping pressure in response to the at least one control signal.

11. The device according to claim 10, further comprising a valve in the inlet line of the dialysate distribution pump, the valve being situated fluidically between the dialysate supply pump and the dialysate distribution pump.

12. The device according to claim 11, wherein the controller controls the predetermined pumping pressure in order to achieve a predetermined valve closure pressure in the inlet line upon closure of the valve.

13. The device according to claim 11, wherein the controller controls a residual pressure in the inlet line of the dialysate distribution pump after completion of an outlet stroke of the dialysate distribution pump in order to achieve a predetermined valve closure pressure in the inlet line upon closure of the valve.

14. The device according to claim 10, wherein the dialysate supply pump is a membrane pump having a pump cavity covered by a flexible membrane, wherein the dialysate supply pump is operable by actuation of the membrane.

15. The device according to claim 14, wherein the dialysate supply pump is pneumatically actuable.

16. The device according to claim 15, wherein the predetermined pumping pressure is controlled by altering a pneumatic pressure applied to the flexible membrane to actuate the dialysate supply pump.

17. The device according to claim 14, wherein a predetermined residual pressure in the inlet line is controlled by altering a pneumatic pressure applied to the flexible membrane after completion of an outlet stroke of the dialysate supply pump.

18. The device according to claim 10, wherein the dialysate supply pump has an inlet stroke in which dialysate is drawn into the dialysate supply pump from a dialysate supply, and an outlet stroke in which dialysate is pumped into the inlet line of the dialysate distribution pump.

19. The device according to claim 10, wherein the controlling means further comprises at least one valve that is arranged to open and close in a dialysate flow path in response to the at least one control signal.

20. The device according to claim 19, wherein the at least one valve comprises at least one of a dialyser inlet valve, a dialyser outlet valve, a dialysate distribution pump inlet valve, and a dialysate distribution pump outlet valve.

21. The device according to claim 1, wherein the pressure sensor is situated in the arterial blood line downstream of a blood pump for pumping blood from the patient to the dialyser.

22. The device according to claim 1, wherein the pressure sensor is situated in the venous blood line.

23. The device according to claim 1, wherein the controlling means comprises a dialysate distribution pump inlet valve that controls pressure in the inlet line by opening and closing in response to the at least one control signal.

24. A method of operating a dialysis machine which has an arterial blood line for delivering patient blood to a dialyser, a venous blood line for returning dialysed blood from the dialyser to the patient, and a dialysate distribution pump for pumping fresh dialysate into the dialyser and spent dialysate out of the dialyser, the dialysate distribution pump having an inlet line for delivering fresh dialysate to the dialysate distribution pump, the method comprising:
converting a sensed pressure to a signal representative of pressure of blood in the arterial blood line and/or pressure of blood in the venous line;
generating at least one control signal in response to the signal representative of the pressure of blood in the arterial blood line and/or the pressure of blood in the venous blood line; and
step for controlling pressure in the inlet line in response to the at least one control signal.

25. The method according to claim 24, wherein the dialysate distribution pump is a flow balance pump for matching volume of dialysate pumped into and out of the dialyser.

26. The method according to claim 25, wherein the flow balance pump has a first pump chamber for pumping dialysate into the dialyser and a second pump chamber for pumping dialysate out of the dialyser.

27. The method according to claim 26, wherein the inlet line of the dialysate distribution pump is fluidically connected to the first pump chamber.

28. The method according to claim 26, wherein the first pump chamber of the flow balance pump has a pump cavity covered by a flexible membrane, and is operable by actuation of the membrane.

29. The method according to claim 26, wherein the second pump chamber of the flow balance pump has a pump cavity covered by a flexible membrane, wherein the pump is operable by actuation of the membrane.

30. The method according to claim 26, wherein the first pump chamber of the flow balance pump has an inlet stroke in which dialysate is drawn from a dialysate supply pump, and an outlet stroke in which dialysate is pumped into the dialyser.

31. The method according to claim 26, wherein the second pump chamber of the flow balance pump has an inlet stroke in which dialysate is drawn from the dialyser and an outlet stroke in which dialysate is pumped to drain.

32. The method according to claim 24, wherein
the dialysis machine further comprises a dialysate supply pump having an outlet fluidically connected to the inlet line of the dialysate distribution pump; and
the controlling step comprises the dialysate supply pump pumping dialysate into the inlet line of the dialysate distribution pump at a predetermined pumping pressure in response to the at least one control signal.

33. The method according to claim 32, wherein the dialysis machine further comprises a valve in the inlet line of the dialysate distribution pump, the valve being situated fluidically between the dialysate supply pump and the dialysate distribution pump.

34. The method according to claim 33, wherein the controlling step further comprises controlling the predetermined pumping pressure in order to achieve a predetermined valve closure pressure in the inlet line upon closure of the valve.

35. The method according to claim 33, wherein the controlling step further comprises controlling a residual pressure in the inlet line of the dialysate distribution pump after completion of an outlet stroke of the dialysate distribution pump in order to achieve a predetermined valve closure pressure in the inlet line upon, before, or at a same time as closure of the valve.

36. The method according to claim 32, wherein the dialysate supply pump has an inlet stroke in which dialysate is drawn into the dialysate supply pump from a dialysate supply, and an outlet stroke in which dialysate is pumped into the inlet line of the dialysate distribution pump.

37. The method according to claim 32, wherein the controlling step further comprises controlling the predetermined pumping pressure by setting a pneumatic pressure applied to a flexible membrane to actuate the dialysate supply pump.

38. The method according to claim 32, wherein the controlling step further comprises controlling a predetermined residual pressure in the inlet line by setting a pneumatic pressure applied to a flexible membrane after completion of an outlet stroke of the dialysate supply pump.

39. The method according to claim 32, wherein the controlling step further comprises operating at least one valve in a dialysate flow path in response to the at least one control signal.

40. The method according to claim 39, wherein the at least one valve comprises at least one of a dialyser inlet valve, a dialyser outlet valve, a dialysate distribution pump inlet valve, and a dialysate distribution pump outlet valve.

41. The method according to claim 24, wherein the controlling step comprises operating a dialysate distribution pump valve in response to the at least one control signal.

42. The method according to claim 24, wherein the controlling step comprises at least one clamp applying compression force to tubing at a specific position along a flow path of the fresh dialysate in response to the at least one control signal.

43. A computer program product embodied on a tangible computer readable storage medium which, when executed by a controller in communication with components of a dialysis machine, causes the controller to generate at least one control signal in response to a signal representative of pressure sensed in an arterial blood line and/or a venous blood line of the dialysis machine;
wherein the arterial blood line is for delivering patient blood to a dialyser of the dialysis machine, and the venous blood line is for returning dialysed blood from the dialyser to the patient;
wherein the dialysis machine comprises a dialysate distribution pump for pumping fresh dialysate into the dialyser and spent dialysate out of the dialyser, the dialysate distribution pump having an inlet line for delivering fresh dialysate to the dialysate distribution pump;

wherein the dialysis machine performs a step for controlling pressure in the inlet line in response to the at least one control signal; and wherein the components of the dialysis machine in communication with the controller comprise one or more components that perform the step for controlling pressure in the inlet line and to which the controller sends the at least one control signal, and comprise one or more components from which the controller receives the signal representative of pressure sensed in the arterial blood line and/or the venous blood line.

* * * * *

UNITED STATES PATENT AND TRADEMARK OFFICE
CERTIFICATE OF CORRECTION

PATENT NO. : 10,960,120 B2
APPLICATION NO. : 14/373591
DATED : March 30, 2021
INVENTOR(S) : Mark Wallace and Ben Higgitt Page 1 of 1

It is certified that error appears in the above-identified patent and that said Letters Patent is hereby corrected as shown below:

In the Specification

In Column 10, Line 21, delete "$P_P$" and substitute therefor --$P_F$--.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*